United States Patent [19]

Nakao et al.

[11] Patent Number: 4,483,855
[45] Date of Patent: Nov. 20, 1984

[54] CEPHALOSPORIN DERIVATIVE AND ANTIBIOTIC COMPOSITIONS

[75] Inventors: Hideo Nakao; Koichi Fujimoto; Sadao Ishihara; Shinichi Sugawara; Isamu Igarashi, all of Hiromachi, Japan

[73] Assignee: Sankyo Company Limited, Tokyo, Japan

[21] Appl. No.: 304,987

[22] Filed: Sep. 23, 1981

[30] Foreign Application Priority Data

Sep. 30, 1980 [JP] Japan .................. 55/136449

[51] Int. Cl.$^3$ .................. A61K 31/545; C07D 501/34
[52] U.S. Cl. ...................................... 424/246; 544/28
[58] Field of Search ......................... 544/28; 424/246

[56] References Cited

U.S. PATENT DOCUMENTS

| | | | |
|---|---|---|---|
| 4,264,595 | 4/1981 | Numata et al. | 424/246 |
| 4,278,793 | 7/1981 | Durckheimer et al. | 544/28 |
| 4,283,396 | 8/1981 | Heymes et al. | 424/246 |
| 4,409,215 | 10/1983 | Takaya et al. | 544/29 |

FOREIGN PATENT DOCUMENTS 0034536  8/1981  European Pat. Off. .............. 544/27

Primary Examiner—Paul M. Coughlan, Jr.
Attorney, Agent, or Firm—Frishauf, Holtz, Goodman & Woodward

[57] ABSTRACT

The compounds of the formula (I):

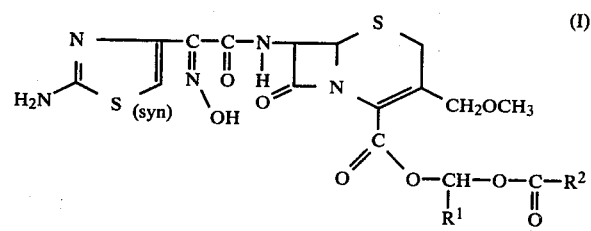

wherein:
 R$^1$ represents a hydrogen atom
and
 R$^2$ represents a —C(CH$_3$)$_3$ group; and pharmaceutically acceptable acid addition salts thereof. The invention also provides antibiotics suitable for oral administration containing at least one of said compound and salts.

4 Claims, No Drawings

CEPHALOSPORIN DERIVATIVE AND ANTIBIOTIC COMPOSITIONS

The present invention relates to a series of new cephalosporin compounds which are particularly suitable for oral administration, to processes and intermediates for preparing these compounds and to compositions containing the compounds.

Although many cephalosporin derivatives which exhibit excellent antibacterial activity have been discovered, most of them are for parenteral administration. However, except where massive doses of an antibiotic are to be administered quickly, the preferred route of administration is oral, as oral preparations can be administered by the patient himself without the need for trained supervision or assistance. Unfortunately, of the many cephalosporin derivatives discovered, very few possess a combination of superior antibacterial activity, broad antibacterial spectrum against both gram-positive and gram-negative bacteria (especially against Staphylococcus aureus) and the ability to be absorbed efficiently through the digestive tract.

For example, cephalothin, cefazolin and cefmetazole are widely used for parenteral administration, particularly by injection. However, when these compounds are administered orally, only about 5% of the dose administered is recovered in the urine, showing their poor absorption through the digestive tract and their unsuitability for oral administration. This is thought to be due to the strong dissociation of the carboxy group at the 4-position (i.e. the low pKa value) and the strong acidity.

Because of this, many efforts have been made to improve the absorption of cephalosporin derivatives through the digestive tract by esterifying the 4-carboxy group but almost all such efforts have failed to obtain cephalosporin derivatives which are well absorbed through the digestive tract and which are therefore useful for oral administration; as described hereafter, in the one instance where absorption through the digestive tract has been significantly improved, the resulting compound lacks the desired broad antibacterial spectrum.

For example, the Journal of Antibiotics, 32 No. 11, 1155 (1979) discloses that the absorption of cefamandol through the digestive tract is not improved by esterification to prepare the acetoxymethyl ester, since this ester is only sparingly soluble in water. Although absorption of the ester through the digestive tract can be improved to a limited extent by administration of the ester in solution in certain organic solvents (such as propylene glycol), this is not a particularly good solution to the problem.

The Journal of Medicinal Chemistry, 22, 657 (1979), on the other hand, reports that the absorption through the digestive tract of another ester of a cephalosporin which is readily soluble in water, is not significantly improved due to chemical instability of the ester.

Furthermore, it is known that, in general, lower alkyl and benzhydryl esters of cephalosporins possess, in themselves, almost no antibacterial activity and that they are not hydrolyzed in vivo (which might otherwise convert them to an active acid) and hence they are not of value for therapeutic use, although they may be useful as synthetic intermediates.

Of the various cephalosporin derivatives known, one known class has a 2-(2-aminothiazol-4-yl)-2-alkoxyiminoacetamido group at the 7-position and may be represented by the following formula:

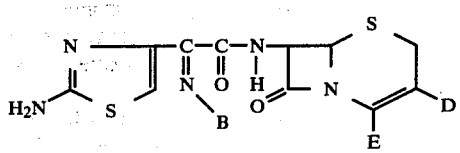

(in which B, D and E are substituents).

For example, Japanese Patent Application Kokai (i.e. as laid-open to public inspection) No. 5046/79 discloses, inter alia, the compound of formula:

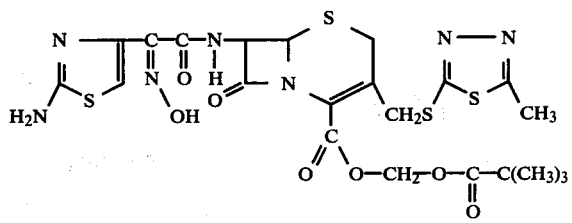

but the recovery rate in urine after oral administration of this compound is only 15%, which is far too low for the compound to be of value for oral administration. Japanese Patent Application Kokai No. 9296/79 discloses, inter alia, a compound of formula:

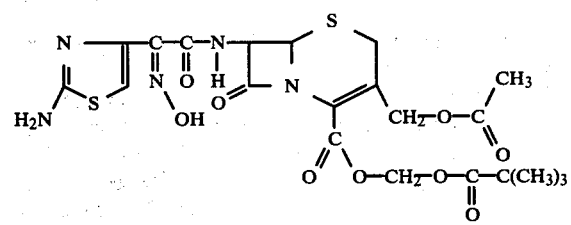

but the recovery rate in urine is expected to be similar to or even less than that of the compound of disclosed in Japanese Patent Application Kokai No. 5046/79.

Another compound having a similar chemical structure, specifically pivaloyloxymethyl 7-[2-(2-aminothiazol-4-yl)-2-methoxyiminoacetamido]-3-methyl-3-cephem-4-carboxylate is disclosed in Japanese Patent Application Kokai No. 34795/78 and we have found that this compound exhibits very good recovery in urine, at a level comparable with that of the compounds of the present invention, thus suggesting that it may well be suitable for oral administration. However, we have also found that this compound, when administered orally, is hydrolyzed and converted in vivo to the corresponding carboxylic acid which, in turn, has poor activity against Staphylococcus aureus. Failure to inhibit the growth of this bacterium, which is perhaps one of the most important from the clinical point of view, could be a disadvantage in actual use.

It is, accordingly, clear from the above discussion that preparation of a cephalosporin derivative which meets the triple requirements of good absorption through the digestive tract, high antibacterial activity and a broad antibacterial spectrum, is not a simple matter. The cephalosporin nucleus includes many points at which different substituents may be introduced and the introduction of a particular substituent to improve one property may adversely affect other properties in a quite unpredictable way. Moreover, it has clearly been demonstrated that, even where a particular chemical modification is known to improve the properties of one particular compound, this is not any indication that a similar modification will similarly improve the properties of any other compound.

We have now surprisingly discovered a limited class of cephalosporin derivatives which can be administered orally, as they are readily absorbed through the digestive tract, and which are then readily hydrolyzed and converted in vivo to the corresponding carboxylic acid which, in turn, shows quite outstanding activity against both gram-positive and gram-negative bacteria.

Accordingly, the present invention consists in compounds of formula (I):

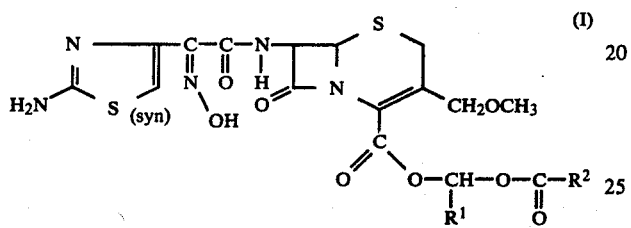

in which:

$R^1$ represents a hydrogen atom or a methyl group; and $R^2$ represents a $C_1$-$C_5$ alkyl group or a $C_1$-$C_5$ alkoxy group;

and pharmaceutically acceptable acid addition salts thereof.

The invention also provides a pharmaceutical composition comprising, as active ingredient, one or more of the compounds of the invention in admixture with a pharmaceutically acceptable carrier or diluent.

The invention also provides a process for preparing the compounds of the invention, as described hereafter.

In the compounds of formula (I) when $R^2$ represents an alkyl group having from 1 to 5 carbon atoms, it is preferably a methyl, ethyl, propyl, isopropyl, butyl, isobutyl, sec-butyl, t-butyl, pentyl, isopentyl or t-pentyl group, most preferably a t-butyl group. $R^2$ most preferably represents an alkyl group having from 1 to 5 carbon atoms when $R^1$ represents a hydrogen atom.

When $R^2$ represents an alkoxy group having from 1 to 5 carbon atoms, it is preferably a methoxy, ethoxy, propoxy, isopropoxy, butoxy, isobutoxy, sec-butoxy, t-butoxy, pentyloxy or 1-ethylpropoxy group, most preferably an ethoxy group. $R^2$ most preferably represents an alkoxy group having from 1 to 5 carbon atoms when $R^1$ represents a methyl group.

Examples of the compounds of the invention are given in the following list: (all of the compounds of the invention have the hydroxyimino group in the syn configuration):

1. Acetoxymethyl 7-[2-(2-aminothiazol-4-yl)-2-hydroxyiminoacetamido]-3-methoxymethyl-3-cephem-4-carboxylate
2. Propionyloxymethyl 7-[2-(2-aminothiazol-4-yl)2-hydroxyiminoacetamido]-3-methoxymethyl-3-cephem-4-carboxylate.
3. Butyryloxymethyl 7-[2-(2-aminothiazol-4-yl)-2-hydroxyiminoacetamido]-3-methoxymethyl-3-cephem-4-carboxylate
4. Isobutyryloxymethyl 7-[2-(2-aminothiazol-4-yl)-2-hydroxyiminoacetamido]-3-methoxymethyl-3-cephem-4-carboxylate
5. Valeryloxymethyl 7-[2-(2-aminothiazol-4-yl)-2-hydroxyiminoacetamido]-3-methoxymethyl-3-cephem-4-carboxylate
6. Isovaleryloxymethyl 7-[2-(2-aminothiazol-B 4-yl)-2-hydroxyiminoacetamido]-3-methoxymethyl-3-cephem-4-carboxylate
7. Pivaloyloxymethyl 7-[2-(2-aminothiazol-4-yl)-2-hydroxyiminoacetamido]-3-methoxymethyl-3-cephem-4-carboxylate
8. Caproyloxymethyl 7-[2-(2-aminothiazol-4-yl)-2-hydroxyiminoacetamido]-3-methoxymethyl-3-cephem-4-carboxylate
9. 1-Methoxycarbonyloxyethyl 7-[2-(2-aminothiazol-4-yl)-2-hydroxyiminoacetamido]-3-methoxymethyl-3-cephem-4-carboxylate
10. 1-Ethoxycarbonyloxyethyl 7-[2-(2-aminothiazol-4-yl)-2-hydroxyiminoacetamido]-3-methoxymethyl-3-cephem-4-carboxylate
11. 1-Propoxycarbonyloxyethyl 7-[2-(2-aminothiazol-4-yl)-2-hydroxyiminoacetamido]-3-methoxymethyl-3-cephem-4-carboxylate
12. 1-Isopropoxycarbonyloxyethyl 7-[2-(2-aminothiazol-4-yl)-2-hydroxyiminoacetamido]-3-methoxymethyl-3-cephem-4-carboxylate
13. 1-Butoxycarbonyloxyethyl 7-[2-(2-aminothiazol-4-yl)-2-hydroxyiminoacetamido]-3-methoxymethyl-3-cephem-4-carboxylate
14. 1-Pentyloxycarbonyloxyethyl 7-[2-(2-aminothiazol-4-yl)-2-hydroxyiminoacetamido]-3-methoxymethyl-3-cephem-4-carboxylate
15. 1-(1-Ethylpropoxycarbonyloxyethyl) 7-[2-(2-aminothiazol-4-yl)-2-hydroxyiminoacetamido]-3-methoxymethyl-3-cephem-4-carboxylate
16. 1-Acetoxyethyl 7-[2-(2-aminothiazol-4-yl)-2-hydroxyiminoacetamido]-3-methoxymethyl-3-cephem-4-carboxylate
17. 1-Propionyloxyethyl 7-[2-(2-aminothiazol-4-yl)-2-hydroxyiminoacetamido]-3-methoxymethyl-3-cephem-4-carboxylate
18. 1-Isobutyryloxyethyl 7-[2-(2-aminothiazol-4-yl)-2-hydroxyiminoacetamido]-3-methoxymethyl-3-cephem-4-carboxylate
19. 1-Pivaloyloxyethyl 7-[2-(2-aminothiazol-4-yl) -2-hydroxyiminoacetamido]-3-methoxymethyl-3-cephem-4-carboxylate
20. Methoxycarbonyloxymethyl 7-[2-(2-aminothiazol-4-yl)-2-hydroxyiminoacetamido]-3-methoxymethyl-3-cephem-4-carboxylate
21. Ethoxycarbonyloxymethyl 7-[2-(2-aminothiazol-4-yl)-2-hydroxyiminoacetamido]-3-methoxymethyl-3-cephem-4-carboxylate
22. Propoxycarbonyloxymethyl 7-[2-(2-aminothiazol-4-yl)-2-hydroxyiminoacetamido]-3-methoxymethyl-3-cephem-4-carboxylate
23. Butoxycarbonyloxymethyl 7-[2-(2-aminothiazol-4-yl)-2-hydroxyiminoacetamido]-3-methoxymethyl-3-cephem-4-carboxylate Of the compounds listed above, particularly preferred compounds are Compounds No. 7 and No. 10.

As indicated in the formula, the compounds of formula (I) of the present invention are in the synconfiguration, which has been found to have much stronger antibacterial activity than the corresponding antiisomers.

The compounds of formula (I) will form acid addition salts with various acids and the invention thus also includes such salts with pharmaceutically acceptable acids, for example inorganic acids (such as hydrochloric acid, sulphuric acid or phosphoric acid) or organic acids (such as methanesulphonic acid, benzenesulphonic acid or malonic acid). Of the acid addition salts, the hydrochlorides are most preferred.

The compounds of formula (I) may be prepared by reacting a corresponding compound of formula (II):

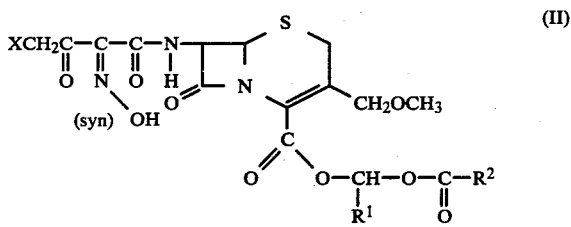

(in which X represents a halogen atom, for example a chlorine or bromine atom, and $R^1$ and $R^2$ are as defined above) with thiourea.

Compounds of formula (II), which are new and also form part of the present invention may be prepared by nitrosoating a compound of formula (III):

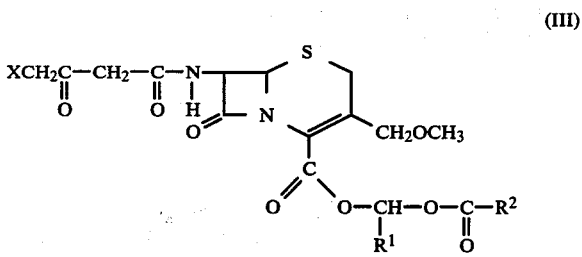

(in which X, $R^1$ and $R^2$ are as defined above).

Accordingly, the compounds of the invention are preferably prepared by a two-stage reaction, in which the compound of formula (III) is first nitrosoated and then the resulting compound of formula (II) is reacted with thiourea to form the thiazole ring.

The nitrosoation of the compound of formula (III) to prepare the compound of formula (II) may be effected by techniques known for the nitrosoation of reactive methylene groups, especially in β-diketones. Such a nitrosoation reaction is normally effected using a metal salt of nitrous acid under acidic conditions or an ester of nitrous acid under suitable conditions. However, when preparing the compounds of the invention, it is necessary to carry out the reaction under such conditions that the cephalosporin ring system and the halogen atom on the side chain at the 7-position do not participate in the reaction. It is, accordingly, desirable to carry out the reaction under weakly acidic or weakly basic conditions at a temperature below ambient. This reaction is normally carried out in the presence of a solvent, the nature of which is not critical, provided that it is capable of dissolving the compound of formula (III) and does not have any adverse effect upon the reaction. Suitable solvents include formic acid, acetic acid, tetrahydrofuran, methanol, ethanol, chloroform, ethyl acetate and benzene, or a mixture of water with one or more of these solvents. The particular solvent chosen will depend upon the nature of the nitrosoating agent.

Examples of metal salts of nitrous acid employed as the nitrosoating agent include alkali metal salts (such as sodium nitrite or potassium nitrite), preferably sodium nitrite. The nitrous acid ester is preferably an ester with a lower alcohol, for example pentyl nitrite or butyl nitrite.

Where a metal salt of nitrous acid is used as the nitrosoating agent, the reaction must be carried out under acidic conditions and, if an acidic solvent (such as formic acid or acetic acid) is not employed, the addition of an acid (which may be organic or inorganic) is necessary. Accordingly, we prefer to carry out the reaction using formic acid or acetic acid as the reaction solvent.

The reaction is preferably carried out at ambient temperature or below and will require a period which may range from 10 minutes to several hours.

After completion of the reaction, the resulting product of formula (II) may be isolated and purified by conventional means, for example by concentration, extraction with organic solvents or chromatographic techniques.

The reaction of the compound of formula (II) with thiourea to give the desired compound of formula (I) is essentially the synthesis of an aminothiazole derivative by reacting a haloketone with thiourea and may be carried out in much the same way as is common for this type of reaction.

The reaction is usually carried out in the presence of a solvent, the nature of which is not critical, provided that it has no adverse effect upon the reaction. The solvent is preferably an organic solvent (such as dimethylformamide, dimethylacetamide, methanol, ethanol, tetrahydrofuran or acetonitrile or a mixture of water with one or more of these organic solvents. If desired, the reaction may be terminated by the addition of a base, for example sodium bicarbonate or potassium bicarbonate.

The thiourea is preferably employed in an amount of 1 or more equivalents per equivalent of said compound of formula (II).

The reaction is preferably effected at ambient temperature and will normally be complete within a period of from 1 to 10 hours.

When the reaction is complete, the desired compound of formula (I) may be isolated and purified by conventional means, for example by concentration, extraction with organic solvents, chromatographic techniques, reprecipitation or recrystallization.

The compounds of formula (I) and their acid addition salts may advantageously be employed in antibacterial composition for oral administration. In order that a compound may be used for this purpose, it is essential, as mentioned above, that it should be well absorbed through the digestive tract after oral administration. Good absorption through the digestive tract is demonstrated by a good recovery of the compound or of degradation products in the urine after oral administration.

The known compound, pivaloyloxymethyl 7-[2-(2-aminothiozol-4-yl)-2-methoxyiminoacetamido]-3-methyl-3-cephem-4-carboxylate has a recovery rate in urine of 66.7%, which is comparable with the value of 50% or more found with pivaloyloxymethyl 7-[2-(2-aminothiazol-4-yl)-2-hydroxyiminoacetamido]-3-methoxymethyl-3-cephem-4-carboxylate, which is representative of the compounds of the present invention. These figures are both quite satisfactory for the purposes of oral administration. However, in addition to this good absorption through the digestive tract, it is desirable that compounds such as the prior art compounds and the compounds of the invention should, after hydrolyzation in vivo, be very active against both gram-positive and gram-negative bacteria. The compounds of the invention, as well as the prior art compound, are hydrolyzed in vivo to the corresponding carboxylic acids and, hence, it is the antibacterial activities of these carboxylic acids, rather than of the esters, which are important from the clinical point of view. The activities of the carboxylic acids corresponding to the above-mentioned prior art compound and the compound of the invention against various bacteria are shown in the following Table, in terms of their minimal inhibitory concentrations (µg/ml).

TABLE

|  | Compound of invention | Prior art compound |
|---|---|---|
| *Staphylococcus aureus* 209P | 0.1 | 12.5 |
| *Escherichia coli* NIHJ | 0.4 | 0.8 |
| *Shigella flexneri* 2a | 0.8 | 0.8 |
| *Klebsiella pneumoniae* 806 | 0.2 | 0.2 |
| *Proteus vulgaris* | 0.2 | <0.1 |
| *Salmonella enteritidis* | 0.4 | 0.4 |

It is clear from the above Table, that the compounds of the invention and the prior art compound, when administered orally, are all highly active against gram-negative bacteria and that their activities against these bacteria are broadly comparable. However, whereas the compound of the invention is highly active against *Staphylococcus aureus*, which is representative of the gram-positive bacteria, the prior art compound has a rather low activity against these bacteria.

The compounds of the invention are preferably administered orally, for example in the form of capsules, tablets, powders, syrups or suspensions. The dosage depends upon the age, symptoms and body weight of the patient and on the duration of treatment, but the dosage may normally range from 0.2 g to 5 g per day, preferably from 0.5 g to 3 g per day for adults; however, if necessary, larger doses may be employed. The compounds are preferably administered in divided doses, for example from 3 or 4 times per day.

In the pharmaceutical compositions of the present invention, any conventional pharmaceutically acceptable carrier or diluent may be employed in admixture with the active compound or compounds. As the composition is generally intended to be administered orally, it is desirably presented in a form readily absorbed through the stomach or intestines. Tablets or capsules are normally in unit dosage form and may contain binding agents (e.g. syrup, gum arabic, gelatin, sorbitol, gum tragacanth, polyvinylpyrrolidone, carboxymethylcellulose or hydroxypropylcellulose), diluents (e.g. lactose, sugar, corn starch, calcium phosphate, sorbitol, glycine, calcium carbonate, calcium phosphate or polyethylene glycol), lubricants (e.g. magnesium stearate, talc, polyethylene glycol or silica), disintegrating agents (e.g. potato starch or carboxymethylcellulose calcium) or wetting agents (e.g. sodium lauryl sulphate) or any combination thereof. The tablets may, if desired, be coated, e.g. with an enteric coating, as is well-known in the art.

Liquid formulations may be aqueous or oily suspensions, syrups, elixirs or similar compositions. Alternatively, the composition may be a dried product which can then be redissolved in water or in another suitable vehicle before administration. Such liquid formulations may contain conventional additives, such as suspending agents (e.g. sorbitol syrup, methylcellulose, glucose/sugar syrup, gelatin, hydroxyethylcellulose, carboxymethylcellulose, aluminium stearate gel or hydrogenated edible fat), emulsifying agents (e.g. lecithin, monooleic acid sorbitol or gum arabic), non-aqueous vehicles (e.g. almond oil, fractionated coconut oil, oily esters, propylene glycol or ethyl acetate) or any combination of two or more thereof.

When the composition of the invention is formulated in unit dosage form, it preferably contains from 50 to 500 mg of the compound or compounds of the invention per unit dose.

The preparation of the compounds of the invention is further illustrated by the following Examples and the preparation of certain intermediates is illustrated by the following Preparations. The compounds of the invention are all in the syn configuration.

PREPARATION 1

Pivaloyloxymethyl 7-bromoacetylacetamido-3-methoxymethyl-3-cephem-4-carboxylate 168 mg of diketene were dissolved in 2 ml of methylene chloride and, whilst stirring the solution, it was cooled to −30° C. To the solution was then added dropwise a solution of 320 mg of bromine in 2 ml of methylene chloride, and the resulting mixture was added dropwise to a solution of 322 mg of pivaloyloxymethyl 7-amino-3-methoxymethyl-3-cephem-4-carboxylate and 299 mg of N,N-diethylaniline in 5 ml of methylene chloride, which had been cooled to −5° C. The mixture was left to stand for 30 minutes, after which it was concentrated by evaporation under reduced pressure. The residue was dissolved in 50 ml of ethyl acetate, washed, in turn, with 5 ml each of water, 5% w/v aqueous hydrochloric acid and a saturated aqueous solution of sodium chloride, and then dried over anhydrous magnesium sulphate. The drying agent was filtered off and the filtrate was concentrated by evaporation under reduced pressure. The residue was chromatographed through a column containing 30 g of silica gel, eluted with a 1:1 by volume mixture of hexane and ethyl acetate, to give 288 mg of the title compound.

PREPARATION 2

Pivaloyloxymethyl 7-(2-bromoacetyl-2-hydroxyiminoacetamido)-3-methoxymethyl-3-cephem-4-carboxylate The whole of the product obtained in Preparation 1 was dissolved in 5 ml of acetic acid. To the resulting solution were added, in small portions, a total of 38 mg of sodium nitrite, whilst stirring the mixture at room temperature. After the addition was complete, stirring was continued for a further 30 minutes. The reaction mixture was then diluted with 20 ml of ethyl acetate, washed three times with a saturated aqueous solution of sodium chloride and dried over anhydrous magnesium sulphate. The drying agent was filtered off and the residue was concentrated by evaporation under reduced pressure. The residue was subjected to column chromatography through 15 g of silica gel, eluted with a 1:1 by volume mixture of hexane and ethyl acetate, to give 200 mg of the title compound.

EXAMPLE 1

Pivaloyloxymethyl 7-[2-(2-aminothiazol-4-yl)-2-hydroxyiminoacetamido]-3-methoxymethyl-3-cephem-4-carboxylate The whole of the product obtained in Preparation 2 was dissolved in 5 ml of dimethylacetamide. To the solution were added 55 mg of thiourea, and the mixture was stirred for 2 hours, after which 20 ml of ethyl acetate were added. The mixture was washed thoroughly with a saturated aqueous solution of sodium bicarbonate to remove the excess thiourea; the mixture was then dried over anhydrous magnesium sulphate, which was then filtered off. The filtrate was concentrated by evaporation under reduced pressure and the residue was subjected to column chromatography through 10 g of silica gel, eluted with ethyl acetate, to give 118 mg of the title compound.

Nuclear Magnetic Resonance spectrum (deuteroacetone) δ ppm: 1.21 (9H, singlet, t-butyl); 3.28 (3H, singlet, $OCH_3$ of methoxymethyl); 3.61 (2H, singlet, 2-cephem $H_2$); 4.27 (2H, singlet, $CH_2$ of methoxymethyl); 5.21 (1H, doublet, J=5 Hz, 6-cephem H); 5.8-6.2 (3H, multiplet, 7-cephem H and $CH_2$ of pivaloyloxymethyl); 6.87 (1H, singlet); 6.4-7.6 (3H, multiplet, $NH_2$ and OH); 9.0 (1H, doublet, J=9 Hz, 7-cephem NH).

EXAMPLE 2

Following the procedure described in Example 1, the following compounds were obtained.

Propionyloxymethyl 7-[2-(2-aminothiazol-4-yl)-2-hydroxyiminoacetamido]-3-methoxymethyl-3-cephem-4-carboxylate.

Nuclear Magnetic Resonance spectrum (deuteroacetone) δ ppm: 1.18 (3H, triplet, J=6.5 Hz, $CH_3$ of propionyl); 2.42 (2H, quartet, J=6.5 Hz, $CH_2$ of propionyl); 3.26 (3H, singlet, $OCH_3$ of methoxymethyl); 3.58 (2H, singlet, 2-cephem $H_2$); 4.28 (2H, singlet, $CH_2$ of methoxymethyl); 5.19 (1H, doublet, J=5 Hz, 6-cephem H); 5.7-6.3 (3H, multiplet, 7-cephem H and $CH_2$ of carbonyloxymethyl); 6.85 (1H, singlet, 5-thiazole H); 6.4-7.6 (3H, multiplet, $NH_2$ and OH); 9.1 (1H, doublet, J=9 Hz, 7-cephem NH).

1-Ethoxycarbonyloxyethyl 7-[2-(2-aminothiazol-4-yl)-2-hydroxyiminoacetamido]-3-methoxymethyl-3-cephem-4-carboxylate.

Nuclear Magnetic Resonance spectrum (deuteroacetone) δ ppm: 1.32 (3H, triplet, $CH_3$ of ethoxy); 1.59 (3H, doublet, $CH_3$ of oxyethyl); 3.30 (3H, singlet, $OCH_3$ of methoxymethyl); 3.59 (2H, broad singlet, 2-cephem H); 4.21 (2H, quartet, $CH_2$ of ethoxy); 4.30 (2H, singlet, $CH_2$ of methoxymethyl); 5.17 (1H, doublet, 6-cephem H); 5.95 (1H, doubled doublet, 7-cephem H); 6.4-7.6 (4H, multiplet, CH of oxyethyl, $NH_2$ and OH); 6.83 (1H, singlet, 5-thiazole H); 8.8 (1H, singlet, 7-cephem NH).

Ethoxycarbonyloxymethyl 7-[2-(2-aminothiazol-4-yl)-2-hydroxyiminoacetamido]-3-methoxymethyl-3-cephem-4-carboxylate.

Nuclear Magnetic Resonance spectrum (deuteroacetone) δ ppm: 1.34 (3H, triplet, J=7 Hz, $CH_3$ of ethoxy); 3.29 (3H, singlet, $OCH_3$ of methoxymethyl); 3.57 (2H, singlet, 2-cephem $H_2$); 4.10-4.40 (4H, multiplet, $CH_2$ of methoxymethyl and $CH_2$ of ethoxy); 5.18 (1H, doublet, J=5 Hz, 6-cephem H); 5.7-6.3 (3H, multiplet, 7-cephem H and $CH_2$ of oxymethyl); 6.83 (1H, singlet, 5-thiazole H); 6.4-7.5 (3H, multiplet, $NH_2$ and OH); 9.2 (1H, doublet, J=9 Hz, 7-cephem NH).

Isovaleryloxymethyl 7-[2-(2-aminothiazol-4-yl)-2-hydroxyiminoacetamido]-3-methoxymethyl-3-cephem-4-carboxylate.

Nuclear Magnetic Resonance spectrum (deuteroacetone) δ ppm: 0.99 (6H, doublet, two $CH_3$ groups of isovaleryl); 1.0-2.1 (1H, multiplet, CH of isovaleryl); 2.3 (2H, multiplet, $CH_2$ of isovaleryl); 3.26 (3H, singlet, $OCH_3$ of methoxymethyl); 3.57 (2H, singlet, 2-cephem $H_2$); 4.26 (2H, singlet, $CH_2$ of methoxymethyl); 5.16 (1H, doublet, J=5 Hz, 6-cephem H); 5.6-6.3 (3H, multiplet, 7-cephem H and $CH_2$ of oxymethyl); 6.86 (1H, singlet, 5-thiazole H); 6.4-7.5 (3H, multiplet, $NH_2$ and OH); 9.0 (1H, doublet, J=9 Hz, 7-cephem NH).

We claim:
1. The compound of the formula (I):

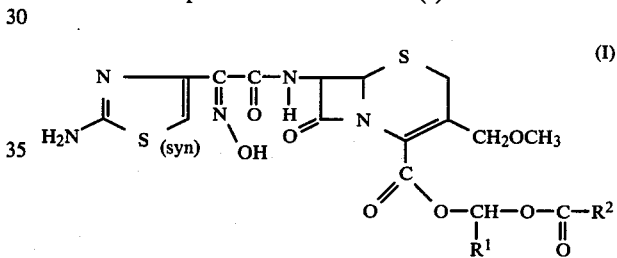

wherein:
$R^1$ represents a hydrogen atom; and
$R^2$ represents a —$C(CH_3)_3$ group; and pharmaceutically acceptable acid addition salts thereof.

2. Pivaloyloxymethyl 7-[2-(2-aminothiazol-4-yl)-2-hydroxyiminoacetamido]-3-methoxymethyl-3-cephem-4-carboxylate of the formula of claim 1.

3. Anti-bacterial pharmaceutical compositions comprising (i) an anti-bacterially effective amount of a compound or salt of claim 1 and (ii) a pharmaceutically acceptable carrier.

4. Anti-bacterial pharmaceutical compositions comprising (i) an anti-bacterially effective amount of the compound of claim 1 and (ii) a pharmaceutically acceptable carrier.

* * * * *